United States Patent [19]

Gaffar

[11] Patent Number: 5,028,439

[45] Date of Patent: Jul. 2, 1991

[54] INHIBITION OF PARATHYROID HORMONE SECRETION

[75] Inventor: Abdul Gaffar, Somerset, N.J.

[73] Assignee: Colgate Palmolive Company, Piscataway, N.J.

[21] Appl. No.: 296,390

[22] Filed: Jan. 9, 1989

Related U.S. Application Data

[63] Continuation of Ser. No. 851,914, Apr. 14, 1986, abandoned, which is a continuation-in-part of Ser. No. 768,394, Aug. 22, 1985, abandoned.

[51] Int. Cl.$^5$ ............................................. A61K 33/42
[52] U.S. Cl. ................................................... 424/601
[58] Field of Search ....................................... 424/601

[56] References Cited

U.S. PATENT DOCUMENTS

| | | | |
|---|---|---|---|
| 4,041,149. | 8/1977 | Gaffar | 424/601 |
| 4,177,258 | 12/1979 | Gaffar et al. | 424/52 |
| 4,183,915 | 1/1980 | Gaffar et al. | 424/52 |
| 4,273,759 | 6/1981 | Gaffar et al. | 424/54 |
| 4,309,410 | 1/1982 | Gaffar | 424/57 |
| 4,430,325 | 2/1984 | Gaffar et al. | 424/601 |
| 4,431,631 | 2/1984 | Clipper et al. | 424/53 |
| 4,537,765 | 8/1985 | Gaffar et al. | 424/53 |
| 4,537,778 | 8/1985 | Clipper et al. | 424/53 |
| 4,547,361 | 10/1985 | Steltenkamp et al. | 424/49 |

OTHER PUBLICATIONS

Textbook of Medicine, 16th Ed. (1982) p. 1336; Cecil.

*Primary Examiner*—Frederick E. Waddell
*Assistant Examiner*—Raymond J. Henley, III
*Attorney, Agent, or Firm*—Robert L. Stone; Murray M. Grill

[57] ABSTRACT

Parathyroid Hormone, when excessively synthesized, induces pathologic bone resorption and demineralization and results in hypocalcemia which produces toxic effects in soft tissues. Non-toxic water-soluble pharmaceutically acceptable compound derivative of peroxydiphosphoric acid, administered orally or systemically, inhibits parathyroid hormone induced bone resorption in vitro and in vivo in warm blooded animals.

4 Claims, No Drawings

INHIBITION OF PARATHYROID HORMONE SECRETION

This application is a continuation of application Ser. No. 06/851,914, filed Apr. 14, 1986, now abandoned which is a continuation-in-part of application Ser. No. 06/768,394 filed Aug. 22, 1985, now abandoned.

This invention relates to inhibition of bone resorption and demineralization caused by excessive secretion of parathyroid hormone (PTH). Such bone resorption and demineralization result in hypocalcemia, which produces toxic effects in soft tissue.

Bone resorption or demineralization can occur directly or indirectly as a result of changes in calcium and phosphate in the body fluids of warm blooded animals.

Normally, PTH is secreted in desired physiological dosages varying for different times as required by the body. It thereby participates in regulating metabolic activities of bone and kidney and the intestinal absorption of calcium in warm blooded animals, such as humans. However, there can be excessive synthesis of PTH such as when primary hyperparathyroidism occurs, which induces pathologic bone resorption and demineralization. The resultant hypocalcemia causes toxic effects in soft tissues.

A particularly important condition in which PTH causes accelerated bone demineralization is osteoporosis, which usually occurs in postmenopausal females (Calcium Tissue Intl. (1983) Vol 35, pages 708–711).

An advantage of the present invention is provision of therapeutic means for inhibiting bone resorption induced by PTH.

Other advantages will be apparent from consideration of the following specification.

In accordance with certain of its aspects, this invention relates to a method for inhibiting parathyroid hormone induced bone resorption comprising administering to a warm blooded mammal host having over-secretion of parathyroid hormone a dosage amount of about 0.16–6 g per kg body weight when said administration is oral or about 0.1–2 g. per kg body weight when said administration is systemic, of a non-toxic water-soluble pharmaceutically acceptable peroxydiphosphate compound to effect contact with said parathyroid hormone.

PTH and its effects are described in *The Role of Calcium in Biological Systems*, Vol. II, Anghileri CRC Press, Boca Raton, Fla., 1981, Chapter II, pages 204–212. PTH is a single chain protein containing 84 amino acids. It may be characterized as PTH (1-84). PTH is synthesized in the body from a precursor called ProPTH which contains 90 amino acids. ProPTH is itself an intermediary material which is synthesized from a protein containing 115 amino acids, called Pre-ProPTH. Typically, warm blooded animals have PTH enzymatically synthesized in a pathway from its precursor materials and then PTH is secreted into the circulation in amounts required by the body. PTH protects organisms from severe hypocalcemia. Thus, when the circulating concentration of ionized calcium is low, the secretion rate of PTH is stimulated.

Metabolic activities of bone, kidney and intestines are directly or indirectly influenced by PTH to increase calcium resorption and phosphate excretion. Bone is particularly effected by PTH in a manner which is time-dependent as well as dose dependent. High doses of PTH initially increase the rate of bone resorption which is followed by increasing the rate of bone formation. There is also an early occurring increase in the net efflux of calcium which is independent of bone resorption.

When PTH secretion is excessive and does not occur in its normal dosage-time related manner responsive to metabolic requirements, undue bone resorption and demineralization occurs, leading to hypocalcemia and toxic effects in soft tissues.

Hydrogen peroxide is known to oxidize methionine groups. Such reaction could be expected to reduce PTH activity. Surprisingly, however, the reduction in PTH activity which is effected by hydrogen peroxide is much less than is effected in accordance with the present invention when a peroxydiphosphate compound is used. Moreover, peroxydiphosphate functions safely, compatibly and efficiently in warm blooded animals, as it is enzymatically degraded by alkaline and acid phosphatases enzymes in accordance with the following equation:

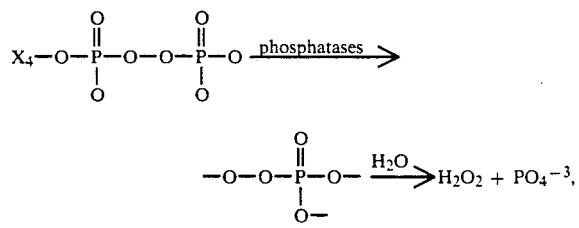

wherein X is a non-toxic pharmaceutically acceptable cation or completes an organic ester moiety. Phosphatase to break down the peroxydiphosphate is present in saliva as well as in plasma, intestinal fluids and white blood cells. The slow oxygen release appears to be particularly effective in inhibiting excessive PTH secretion and thereby reduces the undesirable and toxic effects of excessive PTH secretion.

The peroxydiphosphate compound (PDP) is in the form of a non-toxic pharmaceutically acceptable compound, which goes beyond salts which are described in U.S. Pat. No. 4,041,149. Compounds include alkali metal (e.g. lithium, sodium, and potassium) alkaline earth metal (e.g. magnesium, calcium and strongtium), zinc and tin salts as well as organic peroxydiphosphate $C_{1-12}$ alkyl, adenylyl, guanylyl, cytosylyl and thymylyl esters and also quaternary ammonium and the like salts. Alkali metal, particularly potassium salt is preferred from among the inorganic cations. The tetrapotassium peroxydiphosphate is a stable, odorless, finely divided, free-flowing, white non-hygroscopic crystalline solid having a molecular weight of 346.35 and an active oxygen content of 4.6%.

Tetrapotassium peroxydiphosphate is 47–51% water-soluble at 0° −61° C., but insoluble in common solvents such as acetonitrile, alcohols, ethers, ketones, dimethyl formamide, dimethyl sulfoxide, and the like. A 2% aqueous solution has a pH of about 9.6 and a saturated solution thereof, a pH of about 10.9. A 10% solution in water at 25° C. showed no active oxygen loss after four months, and at 50° C. at 10% solution showed an active oxygen loss of 3% in 6 months.

From among the organic compounds those providing hydrophobic properties such as $C_{1-12}$ alkyl radical and those which facilitate the rapid uptake of peroxdiphosphate moiety by the cells, such as adenylyl, guanylyl, cytosylyl, and thymylyl esters are preferred.

Peroxydiphosphate compound may be administered orally or systemically to inhibit excessive PTH secretion in the body.

Pharmaceutical carriers suitable for oral ingestion are coated tablets composed of material which resists breakdown by gastric acids in the stomach pH (about 1–3) since peroxydiphosphate would be inactivated by such gastric acids. Rather, the carriers, with tableted granules of the peroxydiphosphoric acid salt solid material therein, are dissolved by intestinal fluids which have a higher pH (about 5.5–10) and do not inactivate the peroxydiphosphate, leaving it subject to enzymatic action by phosphatase present in humans or other warm blooded animals. A desirable tablet coating solution is composed of a fatty acid ester such as N-butyl stearate (typically about 40–50, preferably about 45 parts by weight), wax such as carnuba wax (typically about 15–25, preferably about 20 parts by weight), fatty acid such as stearic acid (typically about 20–30 parts, preferably 25 parts by weight) and cellulose ester, such as cellulose acetate phthalate (typically about 5–15, preferably about 10 parts by weight) and organic solvent (typically about 400–900 parts). Other desirable coating materials include shellac and copolymers of maleic anhydride and ethylenic compounds such as polyvinyl methyl ether. Such coatings are distinct from tablets which are broken down in the oral cavity in which the tablet material typically contains about 80–90 parts by weight of mannitol and about 30–40 parts by weight of magnesium stearate.

Tabletted granules of the peroxydiphosphate salt are formed by blending about 30–50 parts by weight of the peroxydiphosphate salt with about 45–60 parts by weight of a polyhydroxy sugar solid such as mannitol and wetting with about 20–35 parts by weight of a polyhydroxy sugar compound solution such as sorbitol, screening to size, blending with about 20–35 parts by weight of a binding agent such as magnesium stearate and compressing the granules into tablets with a tablet compressing machine. The tabletted granules are coated by spraying a foam of a solution of the coating material thereon and drying to remove solvent. Such tablets differ from dental tablets which are typically compressed granules without a special protective coating.

An effective dosage of administration of peroxydiphosphate with a prescribed regimen, when administration is by oral ingestion, is about 0.1–6 g per kg of body weight daily; when administration is systemic, such as by intramuscular, intraperitoneal or intravenous injection, the dosage is about 0.1–2 g per kg of body weight daily.

Physiologically acceptable pyrogen-free solvents are suitable carriers for use in the art-recognized manner for systemic administration. Saline solution buffered with phosphate to a physiological pH of about 7 to 7.4 in the preferred carrier for systemic administration. Such solvents are distinct from water-humectant vehicles typically used in dentifrices. Such solution is typically prepared by sterilizing deionized distilled water, checking to insure non-pyrogenicity using the Limulus amebocyte lysate (LAL) test described by Tsuji et al in "Pharmaceutical Manufacturing", October, 1984, pages 35–41, and then adding thereto a phosphate buffer (pH e.g. about 8.5–10) made in pyrogen-free sterile water and about 1–100 mgs. peroxydiphosphate compound derivative and sodium chloride to a concentration of about 0.5–1.5% by weight. The solution can be packed in vials for use after being resterilized by passing through a micropore filter. As alternatives, other solutions such as Ringer's solution containing 0.86% by weight sodium chloride, 0.03% by weight potassium chloride and 0.033% by weight calcium chloride may be used.

The following example illustrates the ability of peroxydiphosphate (PDP) compound to inhibit release of calcium from bone due to secretion of PTH.

EXAMPLE

Effects of PDP on PTH Induced Bone Resorption in Bone Culture System

The test in which PTH isolated from bovine parathyroid gland (obtained from Bohringer-Mannheim) induces the resorption of bone in a bone culture system is used to assess whether PDP deactivates the bone resorptive activity of PTH. Fetal rat bone culture as described by Raisz, J. Clin. Invest. 44:103–116, 1965, is prepared by injecting rats with $^{45}CaCl_2$ on the 18th day of gestation. The rats are then sacrificed on the 19th day, and radii and ulnae of the embryos, with their cartilagenous ends, are removed and placed for culturing in BGJ medium (Gibco, Buffalo, N.Y.) at 37° C. with 5% $CO_2$. The medium is supplemented with 5% heated (57° C. for 3 hours) fetal calf serum. Bones are placed 4 to a well in 24 well dishes (Nunc, Gibco) containing 0.5 ml of medium per well. The release of $^{45}Ca$ into the culture media from bone incubated in the presence of a test agent is compared with the release from bones incubated in control media, and the results of bone resorption are expressed as a ratio.

PTH is diluted with sterile bovine serum albumin solution. PTH is treated with different concentrations of PDP tetrapotassium salt at 37° C. The excess PDP is removed by dialysis membrane (3,500 mol. wt. maximum). This permits unreactive PDP to diffuse out while the PTH having molecular weight greater than 3,500 is retained inside the bag. The Table below summarizes the data.

| Treatment | No. of Rats | % $^{45}Ca$ Retrieval ± S.D. | Test/Control | Sig. |
|---|---|---|---|---|
| Control (bovine serum albumin) | 6 | 10.63 ± 0.7 | | |
| 1 mcg/ml PTH | 6 | 22.03 ± 3.89 | 2.07 ± 0.37 | |
| 1 mcg/ml PTH + 1000 mcg/ml PDP | 6 | 9.03 ± 2.09 | 0.41 ± 0.09 | 95% |
| 1 mcg/ml PTH + 150 mcg/ml $H_2O_2$ | 6 | 13.68 ± 0.98 | 0.62 ± 0.04 | 95% |

The data in the Table shows that PTH induces bone resorption compared to the control vehicle (bovine serum albumin) (compare 1 vs. 2). PTH treated with PDP significantly reduces bone resorption (compare 2 vs. 3). Moreover, hydrogen peroxide in amount providing an equivalent amount of oxygen to PDP is less effective than PDP in reducing bone resorption caused by PTH (compare 3 vs. 4).

The foregoing results are representative of the effect of PDP tetrapotassium salt and other non-toxic water-soluble pharmaceutically acceptable PDP salts such as other alkali metal salts, alkaline earth metal salts, zinc salt and tin salt as well as $C_{1-12}$ alkyl PDP salts and other organic PDP compounds, particularly including the adenylyl, guanylyl, cytosylyl and thymylyl estersand quaternary ammonium PDP salts in inhibiting PTH secretion in rats and mammals in general.

I claim:

1. A method for inhibiting parathyroid hormone induced bone resorption which comprises administering to a warm blooded mammal host having oversecretion of parathyroid hormone a daily dosage of about 0.1-6 grams per kilogram body weight when said administration is oral, or about 0.1-2 grams per kilogram body weight when said administration is systemic, of a nontoxic water soluble pharmaceutically acceptable potassium salt of peroxydiphosphate.

2. The method claimed in claim 1 wherein said peroxydiphosphate compound is present in amount of about 0.1-7% in a pharmaceutical carrier.

3. The method claimed in claim 2 wherein said peroxydiphosphate compound is present in tabletted granules having a coating thereon which is not broken down during passage through the stomach of said warm blooded animal and which coating is dissolved by intestinal fluids having a pH of 5-10.

4. The method claimed in claim 2 wherein said peroxydiphosphate compound is administered to said warm blooded animal in a solution of non-pyrogenic distilled water and sodium chloride buffered with phosphate.

* * * * *